United States Patent [19]

Gibby

[11] Patent Number: 4,822,594

[45] Date of Patent: Apr. 18, 1989

[54] CONTRAST ENHANCING AGENTS FOR MAGNETIC RESONANCE IMAGES

[76] Inventor: Wendell A. Gibby, 7025 N. Via Assisi, Tucson, Ariz. 85704

[21] Appl. No.: 7,289

[22] Filed: Jan. 27, 1987

[51] Int. Cl.$^4$ .................. A61K 49/00; A61B 6/00; C08B 37/02
[52] U.S. Cl. ............................... 424/9; 536/112; 424/1.1; 436/173; 436/806; 128/653; 128/654
[58] Field of Search .............. 424/1.1, 9; 536/112; 128/653, 654; 436/173, 806

[56] References Cited

U.S. PATENT DOCUMENTS

| | | | |
|---|---|---|---|
| 4,346,216 | 8/1982 | Hinckley | 536/112 |
| 4,639,365 | 1/1987 | Sherry | 424/9 |
| 4,678,667 | 7/1987 | Meares et al. | 424/9 |
| 4,767,611 | 8/1988 | Gordon | 424/9 |
| 4,770,183 | 9/1988 | Groman et al. | 424/9 |

Primary Examiner—Ronald W. Griffin
Attorney, Agent, or Firm—Drucker & Sommers

[57] ABSTRACT

A saccharide matrix containing chelating agents. In a preferred embodiment the chelating agents, for example, EDTA or DTPA, bind metals having at least one unpaired electron. Such compositions are useful for enhancing the contrast of Magnetic Resonance images.

12 Claims, No Drawings

CONTRAST ENHANCING AGENTS FOR MAGNETIC RESONANCE IMAGES

BACKGROUND OF THE INVENTION

1. Field of the Invention

This invention relates to NMR shift reagents and in particular contrast enhancing agents for magnetic resonance imaging.

2. Prior Art

Magnetic Resonance (hereinafter MR) imaging is one of the newest methods of viewing the interior of the human body. Radio waves interact with protons in a magnetic field to produce images having superior contrast compared to X-ray tomography. However, the technique can be non-specific, that is, it may be impossible to distinguish from between many pathological conditions, such as between cancer and the edema surrounding the cancer.

Contrast agents enhance various portions of the MR image by changing, usually decreasing, the relaxation times of the protons in the immediate vicinity to the agent. One example of a contrast agent is that disclosed in the European Pat. No. 3,302,410 of A.G. Schering for gadolinium diethyline triamine pentaacetic acid complex (hereinafter Gd DTPA). Gd DTPA has been attached to a variety of macromolecules, for example monoclonal antibodies, albumin, and dihexadecylamine.

Other agents, such as ethylene diamine tetraacetic acid (hereinafter EDTA), and 1, 4, 7, 10 tetraacetic acid (hereinafter DOTA), have been chelated with Gd in an effort to make a superior contrast agent.

Prior art chelates of Gd, and other paramagnetic metals, suffer from several defects. The body rapidly excretes Gd DTPA, for example. It is not organ specific and stays within the extra-cellular space. As a result, the only organs suitably enhanced with Gd DTPA are kidneys and areas of abnormal brain permeability. Since magnetic resonance imaging requires long data acquisition times rapidly metabolized enhancing agents do not work well.

Another problem with known MR enhancing agents is that the proteins that are used to anchor the simple chelates, monoclonal antibodies and the like, may provoke allergic reactions in the recipient.

It would therefore be advantageous to have a MR contrast enhancing agent that was metabolized slowly in vivo, was organ specific, and did not provoke allergic reactions in the recipient.

SUMMARY OF THE INVENTION

An aspect of this invention is a composition of matter comprising a chelating agent represented by the formula:

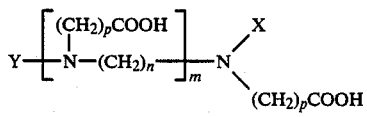

where
m is 1, 2, or 3;
n is an interger between 1 and 4;
p can be independently varied and is an integer between 0 and 2; and
X and Y can be $-(CH_2)_p COOH$ or X is $(CH_2)_n$ and joined to Y;
at least one saccharide bound to said chelating agent through an ester linkage of one of said (COOH) groups and an (OH) group on the saccharide.

A further aspect of this invention is the composition of matter recited above chelated with a paramagnetic metal ion for administration to a patient undergoing MR tomography.

A further aspect of this invention is the method of use of the composition of matter recited above chelated with a paramagnetic metal ion as for enhancing the image formed by MR.

A further aspect of this invention is the method of use of the composition of matter recited above for treating metal poisoning and iron overload states.

A further aspect of this invention is the method of use of the composition of matter of claim 1 for packing ion exchange columns.

DETAILED DESCRIPTION OF THE INVENTION

The chelating agents of this invention are represented by the formula:

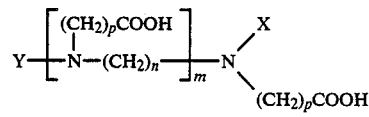

where
m is 1, 2, or 3;
n is an interger between 1 and 4;
p can be independently varied and is an integer between 0 and 2; and
X and Y can be $-(CH_2)_p$ COOH or X is $(CH_2)_n$ and joined to Y;

Examples of chelating agents in this category include DTPA (where m is 2, n is 2, each p is 1 and x and y are $-(CH_2)_p$ COOH); EDTA (where m is 0, n is 2, and each p is 1 and x and y are $-(CH_2)_p$ COOH) and DOTA (where m is 3, n is 2, each p is 1, x is $-(CH_2)_2-$ and joined to y. These agents are known to tenaciously bind metal ions. They can be used to place otherwise toxic metal ions in organic environments, particularly biological environments by coordinating with the metal ion and thus preventing it from poisoning critical membranes or enzymes.

As used herein "saccharide" will refer to monosaccharides such as glucose and maltose and the like, polysaccharides, such as dextran and glycogen, and the like, and reduced sugars, such as mannitol, and the like.

As used herein, "chelate/saccharide" will refer to the compounds formed by the reaction of the above described chelates with the above described saccharides. The carbonyl or (COOH) groups at the various terminii of the chelating agent can react with the hydroxyl or (OH) groups on the saccharide, thereby forming ester linkages. Since the chelate has more than one (COOH) group and the saccharide have more than one (OH) group, large cross linked polymers may be formed.

Metal ions easily bind to the chelate/saccharide. Preferred metal ions include those having at least one unpaired electron, which is to say, those that are paramagnetic. Examples include Cr, Mn, Fe, Co, and the lanthanide metals, particularly Gd, Dy, and Tc.

The metal complexes of the chelate/saccharides can then be used as contrast enhancers for MR images. The method of administration of the complex, depends on the portion of the anatomy to be imaged. For example, if the gastrointestinal tract is to be imaged, oral administration is preferred. For imaging of the liver, spleen, and kidneys, intravenous administration is preferred.

Various formulations of the metal chelate/saccharide will have different physical properties. For example, highly cross-lined polymeric chelate/saccharide will be fairly insoluble particles, but less highly cross linked polymers are more soluble. The amount of cross linking can be controlled by the ratio of chelate to saccharide. The ratio will range from about 2:1 to about 1:50. In general, the more chelate present the more the product will be cross linked.

Another physical variable that can be controlled is the size, or molecular weight, of the saccharide. Small saccharides, such as monosaccharides and oligosaccharides, produce more easily soluble chelate/saccharide. Larger saccharides, such as high molecular weight dextran, or starch, produce more insoluble chelate/saccharide.

The clinician can use the various properties to his advantage. For example, if the area to be imaged includes delicate vascular systems, for example, the liver, or brain, a highly soluble form of metal chelate/saccharide is preferred. If double contrast images of gastrointestinal tract are preferred, then more insoluble form of metal chelate/saccharide that coats the interior surface of the organs is preferred.

The chelate/saccharide without a bound metal ion can be used as an antidote in metal poisoning. The toxic metals tend to build up in the liver, and since the chelate/saccharide is metabolized in the liver, the chelate scavenges the excess toxic metal.

When used as magnetic reasonance image enhancer, or as a poison antidote, the chelate/saccharide may be formulated with an excipient, for example, unreacted saccharide, emulsifiers, solvents, such a saline solution, or the like, may be added by methods well known in the art.

The chelate/saccharide can also be used for ion exchange column packing. The physical properties of the chelate can be varied to more favorably bind one metal ion than another another, thereby giving the column the desired discrimination.

Methods of Preparation

The chelate/saccharides of the present invention are prepared as follows:

The chelate-bisanhydride is prepared by adding dry chelate to an anhydrous organic base, for example, pyridine, lutidine, piperidine, or the like. The resulting slurry is stirred and an anhydrous organic acid, for example, acetic acid or peutanoic acid, is slowly added.

The mixture is heated to about 45° C. to about 85° C. preferably about 65° C. and left for between 12 hours and 48 hours preferably about 20 hours. The liquid is filtered, and the solid material is washed with the same organic acid used before.

The ratio of chelate to saccharide ranges from 2:1 to 1:50 when the saccharide is calculated as glucose. The average number of glucose units in a given polymer must therefore be known. The saccharide and the chelate are mixed dry in, for example, a beaker. Anhydrous dimethyl sulfoxide (DMSO) is added to the thoroughly mixed dry mixture.

The next step provides a choice of physical properties depending on whether a gel-like consistency is desired or if fine particles are desired.

The gel is obtained by warming the DMSO mixture until the particles go into solution. Typically this temperature is from 40° C. to 70° C. The gel is purified by dialysis in water.

Particles are obtained by pulverizing the mixture with a homogenizer. The homogenized mixture is let stand for several hours, then the supernatant is decanted off.

After the chelate/saccharide is obtained, a metal ion can be added to form a complex. A metal halide, for example gadolinium chloride, is added to an aqueous suspension, and the mixture is mixed well. After dialysis, the resulting solid is dried.

EXAMPLES

Example 1

DTPA Bis-anhydride 80 grams of DTPA dried overnight at 70° was added to 100 ml of anhydrous pyridine (Aldrich Chemical Co., St. Louis, MO). The resultant slurry was stirred while 76 ml of anhydrous acetic acid was slowly added over several minutes. This was heated to 65° and left for 20 hours. Then the liquid was filtered off through a fritted glass filter. The resulting solid white material was washed five times with anhydrous acetic acid until no more amber color was eluted. Then the clean solid white material was washed three times with anhydrous ether. The DTPA bis-anhydride was dried at 65° C. overnight.

Dextran DTPA polymer

Dextran of an average molecular weight of 100,000 to 200,000, with an assumed average molecular weight of 150,000, was reacted with DTPA Bis-anhydride in various molar ratios of DTPA to glucose units.

Example 2

High Molecular Weight

A DTPA to glucose ratio of 10:1 was selected. 12.5 grams of dextran which had been dried overnight in an oven at 70° was added to 2.5 grams of DTPA Bis-anhydride and stirred dry within a beaker. 100 ml of DMSO, which had been previusly dried over calcium hydride and filtered through whatman #2 filter paper, was then added. This was heated with stirring to 60° C., whereupon the solution cleared and became a gel-like material. Neither dextran with DMSO and heating nor DTPA and DMSO with heating yielded a similar gel. The total volume was brought to 250 ml with water. This was homogenized with a Virtis model 45 double blade blender for one minute at high speed. This was dialyzed against five gallons of water which was changed daily for two days in standard dialysis bags (Union Carbide). DTPA/dextran was isolated.

Similarly, by substituting EDTA or DOTA for DTPA one can obtain the EDTA/dextran polymer and the DOTA/dextran polymer.

Example 3

Gadolinium Chelate of High Molecular Weight 0.9 grams of gadolinium chloride (Morton Thiokol Corp.) was added to the product of Example 2. The material was mixed well, then dialysed for an additional two days against five gallons of water with the water changed daily. 100 cc's of absolute ethonal was then added. The substance was rotovaped at 80° C. with a Bruker flash evaporator to dryness. The material was then left in a dessicator. With reconstitution in water, the substance formed a viscous clear solution.

Similarly, by substituting chromium chloride, manganese chloride, iron chloride, cobalt chloride, dysprosium chloride, or technetium pertechnetate in the presence of stannous ion for gadolinium chloride one can obtain the chromium DTPA/dextran chelate; the manganese DTPA/dextran chelate; the iron DTPA/dextran chelate; the cobalt DTPA/dextran chelate; the dysprosium DTPA/dextran chelate; and the technetium DTPA/dextran chelate.

Example 4

Dextran particulate preparation

A 1:1 ratio of glucose units to DTPA was selected. 25 grams of DTPA bis-anhydride was added to 12.5 grams of dextran with an average molecular weight of 150,000. This was mixed dry and reacted in anhydrous DMSO for 10 hours at 65° C. This was then homogenized with 150 ml of water for one minute with a Virtis double blade model #45 homogenizer. After sitting for several hours the supernatant was decanted off. The resulting insoluble particles were added to 500 ml of water and mixed. This was centrifuged at 2,000 RPM, the fluid decanted off and the wash and centrifugation was repeated with an additional 500 ml of water. The particles at this point were approximately 100–1,000 microns when visualized under a microscope. The DTPA-dextran particles were then isolated.

Similarly, by substituting EDTA or DOTA for DTPA one can obtain the EDTA/dextran polymer and the DOTA/dextran polymer.

Example 5

Gadolinium Chelate 3.44 grams of gadolinium chloride was added to the product of Example 4 and the particulate suspension was mixed well with 100 ml of water. The substance was then washed and centrifuged with 500 ml of water three times as above. The material was then lyophilized and placed in a dessicator. A small amount was heated to boiling in a 50 ml beaker of water without dissolution. The particles swelled slightly with heating.

A small aliquot of the particles were then ground with a mortar and pestal and suspended in water. At this point, the particle size was 10–500 microns under a microscope. A small amount was then homogenized at maximum speed with a Tekmar Ultraturrax homogenizer for five minutes. The particle size was mostly 5–200 microns with some particles ranging up in size to 500 microns. The suspension was then allowed to settle leaving a cloudy particulate suspension in solution with particle size from 0–100 microns that was decanted off. A 1 ml aliquot of this was placed in a beaker which was dessicated for two days in an oven at 70° C. The resulting weight demonstrated a concentration of weight per volume of particles of 8 mg/ml.

Subsequent to this, 10 ml of the material was filtered through a 10 micron nylon mesh with a resulting concentration of 3.5 mg/ml as indicated by dry weight analysis. The material was gadolinium DTPA/dextran particles.

Similarly, by substituting chromium chloride, manganese chloride, iron chloride, cobalt chloride, dysprosium chloride, or technetium pertechnetate in the presence of stannous ion for gadolinium chloride one can obtain the chromium DTPA/dextran chelate; the manganese DTPA/dextran chelate; the iron DTPA/dextran chelate; the cobalt DTPA/dextran chelate; the dysprosium DTPA/dextran chelate; and the technetium DTPA/dextran chelate.

Example 6

Medium Molecular Weight Dextran - DTPA

Dextran of an average molecular weight of 17,000 was reacted with DTPA in a ratio of 1 DTPA to 2 glucose units. 10 grams of DTPA bis-anhydride was mixed dry with 10 grams of anhydrous dextran. This was then stirred and gently heated in 100 ml of DMSO. An amber jelly formed. Stirring broke up the jelly and 100 ml of distilled water was added. This was placed in a dialysis bag and dialysed against five gallons of distilled water. The dialysis was changed twice over two days. This was then rotovaped with 100 cc's of ethanol at 80°. The resulting amber crystals weighed 14 grams. mp =175° C. Decomposition.

Similarly, by substituting EDTA or DOTA for DTPA one can obtain the EDTA/dextran polymer and the DOTA/dextran polymer.

Example 7

DTPA Dextrose and Maltose

The synthesis was carried out with a molar ratio of 1 DTPA to 4 glucoses units. 9 grams of DTPA bis-anhydride plus 18 grams of anhydrous glucose were mixed and heated in 100 ml of DMSO which had been previously dried over calcium hydride and filtered. This solution was stirred until it became a clear amber color. This was cooled and 400 cc's of 100% ethanol was added. A precipitate formed which was filtered and the filtrate was discarded. The precipitate was taken up in 50 ml of water heated and filtered. 50 ml of 100% ethanol was added and the cloudy mixture was heated until clear. This was cooled in the refrigerator. The tarry residue which precipitated out was removed from the bottom of the beaker. The residue was then dissolved in 20 ml of water and the pH adjusted to 7.0 with 1 N NaOH. The solution was then dessicated over drierite. The weight obtained of crystals was 3.0 grams. Mass spectroscopy confirmed a product with a m.w. of 717 corresponding to the bis-gluco-DTPA.

DTPA maltose was formed in a similar fashion using 9 grams of maltose (dried in an oven for four days at 65°) and 9 grams of DTPA bis-anhydride. mp 165° C.

IMAGING EXPERIMENTS USING IMAGING CONTRAST ENHANCEMENT

Experimental Rat

Sprague Dawley albino type rats weighing approximately 250 grams were used for all the MR imaging experiments. Sedation was perfomed by using an initial injection of intraperitoneal pentobarbitol at 50 milligrams/kilograms and then maintained with an intraperitoneal catheter with intermittent pentobarbitol injections. The rats were immobilized in the imager using a plexiglass tube into which the rat was inserted, with the feet taped to the side of the tube. All intravenous injections were performed through a cut down line inserted into the internal jugular vein. The oral solutions were administered via a small nasogastric cannula.

Control Rat

Control images were performed through the heart and liver of a rat prior to the injection of contrast material. Subsequent to this, five cc's of dextran of the 100-200,000 average molecular weight (NBC, Cleveland, OH) in a concentration of 3 grams/100 cc's was injected intravenously. As expected, there was no significant enhancement following the dextran injection. The rat was subsequently sacrificed with an overdose of intraperitoneal anesthesia. Images of the rat were then obtained through the heart and liver which again showed no significant contrast enhancement of organs or blood.

Example 8

Gadolinium DTPA Dextran 150,000/10:1

A rat was given 5 cc's intravenously of the gadolinium DTPA dextran 10:1 polymer, the product of Example 2, which was in a concentration of 3 grams per 100 cc's of distilled water. Contrast enhancement of the liver and kidneys was well demonstrated at 2.5, 3.0, and 3.5 hours after contrast injection. The enhancement of both kidneys and liver appeared to increase over time being best seen on the 3.0 and 3.5 hour images.

Example 9

A rat was then injected with 5 ml of gadolinium DTPA dextran 150,000 molecular weight polymer 10:1. The rat was then sacraficed an hour and 45 minutes later. Images through the heart, pulmonary vasculature, aorta, inferior vena cava and liver showed significant residual contrast material within the non-flowing blood. This demonstrates that if compensation could be made for flow, there is significant contrast material present even at 1.75 hours to allow visualization of blood vessels.

Example 10

Gadolinium DTPA dextran used as an oral contrast agent

Gadolinium dextran DTPA polymer from the 150,000 molecular weight dextran starting material in a ratio of 5 glucose molecules to 1 DTPA molecule, prepared according to Example 2, was reconstituted into an approximately isotonic gel with 0.7 grams of the gadolinium DTPA/dextran per 30 ml of water. Five ml of this solution was injected via nasogastric tube into the stomach. Serial images were obtained of the stomach and intestines. Execellent contrast opacification of the samll bowel was observed. Contrast lining the walls of the stomach was observed.

Example 11

Gadolinium dextran particles used for embolization

Gadolinium dextran particles in a 1:1 ratio of DTPA to glucose using the 150,000 molecular weight dextran were prepared according to Example 5. The non-filtered variety were used, the particle sizes ranging from 1-100 microns by light miscroscopy. Five ml of particles in a concentration of approximately 5 mg/ml were injected. The rat died shortly after the injection. The resultant MR images demonstrate contrast enhancement of the cardiac chambers and major blood vessels. Opacification was observed of even the small subclavian arteries. This demonstrates that the particles could be used for embolo thereapy with subsequent visualization using MR Imaging of the infarct.

Example 12

Gadolinium DTPA Dextran Particles 10 microns

The gadolinium DTPA dextran particles of Example 5 were filtered through a 10 micron nylon mesh with a resulting concentration of approximately 3 mg/ml. A rat was then injected with 5 ml and serial images were obtained. The rat was allowed to live for 24 hours with serial images taken. Then animal was then sacrificed. Images at 3 hours demonstrates execellent opacification of the pyelocaliceal system of the right kidney. Little residual contrast was seen in the liver in the images approximately 24 hours after the injection.

I claim:

1. A chelating agent represented by the formula:

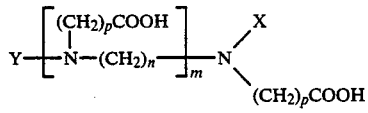

where
m is 1, 2, or 3;
n is an interger between 1 and 4;
p can be independently varied and is an integer between 0 and 2; and
X and Y can be —$(CH_2)_p$ COOH or X is $(CH_2)_n$ and joined to Y;
at least one saccharide is bound to said chelating agent through an ester linkages of one of said (COOH) groups and (OH) groups of the saccharide.

2. A composition of matter comprising the chelating agent of claim 1 and a metal ion having at least one unpaired electron chelated to said chelating agent.

3. The compound of claim 1 wherein said chelating agent is selected from the group of EDTA, DTPA, and DOTA.

4. The compound of claim 3 wherein said saccharide is selected from dextran, glucose and maltose.

5. The compound of claim 4 wherein said saccharide is a polymer and said saccharide is bound to said chelating agent through at least two ester linkages.

6. The compound of claim 2 wherein said metal ion is selected from the lanthanide group of metals.

7. The compound of claim 6 wherein said metal ion is Gd.

8. The compound of claim 2 wherein said metal ion is selected from the group consisting of Cr, Mn, Fe and Co.

9. A composition of matter comprising the chelating agent of claim 1 and an excipient for administration to a patient for MR tomography.

10. A method of enhacning MR contrast in a living subject, comprising administering internally to the subject an effective amount of a contrast agent which comprises the chelating agent of claim 1.

11. A method for the treatment of heavy metal poisoning in a living subject, comprising administering internally to the subject an effective amount of the chelating agent of claim 1.

12. A method for producing ion exchange columns which comprises employing the chelating agent of claim 1 as the ion exchange column packing.

* * * * *